(12) United States Patent
May et al.

(10) Patent No.: US 10,279,305 B2
(45) Date of Patent: May 7, 2019

(54) METHOD FOR GAS SEPARATION

(71) Applicants: The University of Western Australia, Nedlands (AU); Chevron U.S.A. Inc., San Ramon, CA (US)

(72) Inventors: Eric Freemantle May, Crawley (AU); Gang Li, Crawley (AU); Kaman Ida Chan, San Ramon, CA (US); Stanley Hsing-Wei Huang, San Ramon, CA (US); Thomas Leroy Hinton Saleman, Göteborg (SE)

(73) Assignees: The University of Western Australia, Crawley, Western Australia (AU); Chevron U.S.A. Inc., San Ramon, CA (US)

( * ) Notice: Subject to any disclaimer, the term of this patent is extended or adjusted under 35 U.S.C. 154(b) by 13 days.

(21) Appl. No.: 15/566,434

(22) PCT Filed: Apr. 15, 2016

(86) PCT No.: PCT/AU2016/000129
§ 371 (c)(1),
(2) Date: Oct. 13, 2017

(87) PCT Pub. No.: WO2016/164963
PCT Pub. Date: Oct. 20, 2016

(65) Prior Publication Data
US 2018/0104640 A1    Apr. 19, 2018

(30) Foreign Application Priority Data
Apr. 15, 2015   (AU) ................................. 2015901358

(51) Int. Cl.
*B01D 53/047*   (2006.01)
*C07C 7/13*   (2006.01)
(Continued)

(52) U.S. Cl.
CPC .............. *B01D 53/047* (2013.01); *C07C 7/13* (2013.01); *C10L 3/105* (2013.01);
(Continued)

(58) Field of Classification Search
None
See application file for complete search history.

(56) References Cited

U.S. PATENT DOCUMENTS

| 5,406,802 A | 4/1995 | Forte | |
| 9,943,799 B2 * | 4/2018 | Rota | .................... B01D 53/047 |
| 2011/0005392 A1 | 1/2011 | Pirngruber et al. | |

FOREIGN PATENT DOCUMENTS

WO    2014128048 A1    8/2014

OTHER PUBLICATIONS

International Search Report and Written Opinion for PCT/AU2016/000129 dated Jun. 16, 2016.

* cited by examiner

*Primary Examiner* — Tam M Nguyen
(74) *Attorney, Agent, or Firm* — Hunton Andrews Kurth LLP (57) ABSTRACT

A method for controlling gas separation of a gas mixture comprising a first component and a second component, the method comprising contacting a feed containing the gas mixture with an adsorbent in a bed in a column in a dual reflux swing adsorption process such that a first component of a gas mixture attains or exceeds a desired purity and a second component of the gas mixture attains or exceeds a desired purity, wherein the mathematical product of the cycle feed time and the sum of the molar feed flow rate and the molar reflux flow rate directed to the column does not exceed the maximum number of moles that can be treated per bed per cycle and wherein the ratio of the first product flow rate to the feed flow rate is less than or equal to the first (Continued)

component's fraction of the feed, and the ratio of the second product flow rate to the feed flow rate is less than or equal to the second component's fraction of the feed.

15 Claims, 5 Drawing Sheets

(51) Int. Cl.
*C10L 3/10* (2006.01)
*B01D 53/04* (2006.01)

(52) U.S. Cl.
CPC .... *B01D 53/0462* (2013.01); *B01D 2253/102* (2013.01); *B01D 2253/108* (2013.01); *B01D 2253/116* (2013.01); *B01D 2256/245* (2013.01); *B01D 2257/102* (2013.01); *B01D 2258/05* (2013.01); *B01D 2259/402* (2013.01); *B01D 2259/40045* (2013.01); *B01D 2259/40062* (2013.01); *C10L 2290/542* (2013.01)

METHOD FOR GAS SEPARATION

CROSS-REFERENCE TO RELATED APPLICATIONS

The present application is a National Stage Application of PCT/AU2016/000129, filed Apr. 15, 2016, hereby incorporated by reference, which claims priority to Australian Application Number 2015901358, filed on Apr. 15, 2015.

TECHNICAL FIELD

A method for controlling gas separation using dual reflux swing adsorption.

BACKGROUND ART

The following discussion of the background art is intended to facilitate an understanding of the present invention only. The discussion is not an acknowledgement or admission that any of the material referred to is or was part of the common general knowledge as of the priority date of the application.

Pressure swing adsorption (PSA) is an established technology employed to separate gas mixtures by exploiting differences in the adsorption capacities of the constituent gases, or, in a few industrial examples, by exploiting differences in sorption rates to achieve a kinetic selectivity. A continuous adsorption process can be realised with multiple beds operating in cycles of high-pressure adsorption steps and low-pressure regeneration or desorption steps together with intermediate bed pressurisation steps. Such a stripping-type PSA process can be designed by selecting an appropriate adsorbent, operating pressures, flow regime and step durations to remove methane from nitrogen or air to a very low concentration (e.g. <100 ppmv). However, one limitation in the application of PSA to gas purification is that few PSA designs can produce both a high-purity light product (raffinate) from the adsorption steps and an enriched secondary product (extract) during the regeneration steps.

The dual reflux PSA (DR-PSA) processes (also known as duplex PSA) combines the stripping and enriching PSA cycles into a single system with at least two beds where the feed gas is fed to an intermediate position along the adsorbent bed and some of each product stream is refluxed into the respective ends of the two adsorption columns. Dual reflux PSA processes have features similar to a continuous distillation process; for example when both gas species are competing for adsorption sites the phase equilibria (vapor-solid) is akin to vapor-liquid equilibria, and the use of light and heavy refluxes through the adsorbent beds is similar to the use of vapor and liquid refluxes in a distillation process.

SUMMARY OF INVENTION

In accordance with one aspect of the present disclosure, there is provided a method for controlling gas separation of a gas mixture comprising a first component and a second component, the method comprising contacting a feed containing the gas mixture with an adsorbent in a bed in a column in a dual reflux swing adsorption process such that a first component of a gas mixture attains or exceeds a desired purity and a second component of the gas mixture attains or exceeds a desired purity, wherein the mathematical product of the cycle feed time and the sum of the molar feed flow rate and the molar reflux flow rate directed to the column does not exceed the maximum number of moles that can be treated per bed per cycle and wherein the ratio of the first product flow rate to the feed flow rate is less than or equal to the first component's fraction of the feed, and the ratio of the second product flow rate to the feed flow rate is less than or equal to the second component's fraction of the feed.

In the context of the present disclosure, the term mathematical product of the cycle feed time and the sum of the molar flow rates of the feed and reflux is also referred to as the product of the cycle feed time and the sum of the molar flow rates of the feed and reflux.

Advantageously, the method of the present disclosure may be utilised to obtain an optimum gas separation, as defined herein.

In one embodiment, the first component is a heavy component and the second component is a light component.

In one embodiment, the product of the cycle feed time and the sum of the molar flow rates of the feed and reflux directed to the feed column is maintained as close as possible to the maximum number of moles that can be treated per bed per cycle.

In one embodiment, the product of the cycle feed time and the sum of the molar flow rates of the feed and reflux directed to the feed column is maintained as close as possible to, but without exceeding, the maximum number of moles that can be treated per bed per cycle.

It will be appreciated that where the product of the cycle feed time and the sum of the molar flow rates of the feed and reflux directed to the feed column equals the maximum number of moles that can be treated per bed per cycle, the method will provide the maximum degrees of productivity attainable for the first and second components, also referred to as the optimum gas separation.

In one embodiment, the ratios of the product flow rates to the feed flow rates are maintained at the same values as the corresponding fractions of the target components in the feed mixture composition.

Preferably, the reflux flow rate is a sufficiently large fraction of the feed flow rate such that both the enrichment factor for the heavy component (amount of heavy component in heavy product divided by that in the feed composition) and/or the stripping factor for the light component (amount of heavy component in the feed composition divided by that in the light product) are both no less than the pressure ratio used in the process. Advantageously, this provides both high purity and recovery for the products.

In one embodiment, the reflux flow rate is 0.5 or more of the feed flow rate.

Embodiments of the present disclosure may be performed using any known adsorption technique such as pressure swing adsorption, thermal swing adsorption, displacement purge or nonadsorbable purge (i.e. partial pressure reduction), dual reflux adsorption, or combination of the above.

Embodiments of the present disclosure may use a wide range of gas sources, such as natural gas, coal mining gas, coalbed methane (coal seam methane), biogas, ventilation air in coal mines and LNG vent gas. Near 50% binary mixtures (e.g. coal mining gas, biogas) can be treated to increase the concentration of the methane component. Gas streams containing as little as 0.5-5% methane (e.g. ventilation air in coal mines or LNG vent gas) may be purified by the method of the invention down to 100 ppm methane. Embodiments of the present disclosure can also be used to reject nitrogen from sub-quality natural gas (e.g. enriching 75% methane to 90% as desired for gas-processing and LNG production).

It will be appreciated that any adsorbent with a selectivity (equilibrium, kinetic, or steric) for methane over nitrogen ($CH_4$ over $N_2$) that is different than 1 may be utilised. Adsorbents with equilibrium selectivity for $CH_4$ over $N_2$ include activated carbons, zeolites and ionic-liquidic zeolites.

In one embodiment, an adsorbent is used having an equilibrium selectivity for $CH_4$ over $N_2$ greater than 2.

In one embodiment the adsorbent is TMAY-Y, a tetramethyl ammonium exchange Y-type zeolite as described in International Patent Application PCT/AU2015/000588 incorporated herein by reference.

In one embodiment, the adsorbent has an equilibrium selectivity for $CH_4$ over $N_2$ greater than 5.

It will be appreciated that when using kinetically-selective adsorbents, like carbon molecular sieves and clinoptilolite for which there is a (relatively long) time-scale required for appreciable adsorption of a given component (characteristic sorption time), the cycle feed time also needs to be shorter than the characteristic sorption time of the less-adsorbed component.

In one embodiment, the adsorbent material is kinetically selective for the gas mixture component that is more adsorbed during the DR-PSA cycle.

In one embodiment, the feed step time is chosen to be shorter than the characteristic sorption time of the slower and less adsorbed gas component but longer than the characteristic sorption time of the faster and more adsorbed gas component.

In one embodiment, the adsorbent is kinetically selective for nitrogen over methane.

It is desirable to utilise a pressure swing adsorption process at a temperature and pressure effective for adsorption and desorption of methane, with the temperature preferably maintained in the range −50° C. to 100° C., and more preferably from 0° C. to 70° C. The pressure during adsorption is preferably between about 10 psi to 100 psi. The pressure during desorption is lower than during adsorption and is effective to cause the desorption of methane, preferably from about 0.1 torr to 150 psi, more preferably from about 0.1 torr to about 50 psi and most preferably from about 0.1 torr to about 25 psi.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

DESCRIPTION OF EMBODIMENTS

The applicant has identified a process for optimising gas separation using a DR-PSA cycle for a given capital and operational cost. This description will utilise the separation of $N_2$—$CH_4$ mixtures by DR-PSA by way of an example to illustrate an embodiment of the invention.

A typical DR-PSA cycle includes four basic steps: feed (FE), purge (PU), pressurization (PR) and blow down (BD), which occur in the pairs FE/PU and PR/BD so that every half-cycle is symmetric with each column's state swapping during the second half. The cycle can be configured so that the feed stream enters either the high pressure (PH) column or the low pressure (PL) column. Similarly, the cycle can be configured so that the pressure inversion is carried by transferring gas between the ends of the columns that is rich in either the heavy (more adsorbed) component (A), or in the light (less adsorbed) component (B). This leads to the four DR-PSA configurations, referred to as PH-A, PH-B, PL-A and PL-B.

Figure 1:
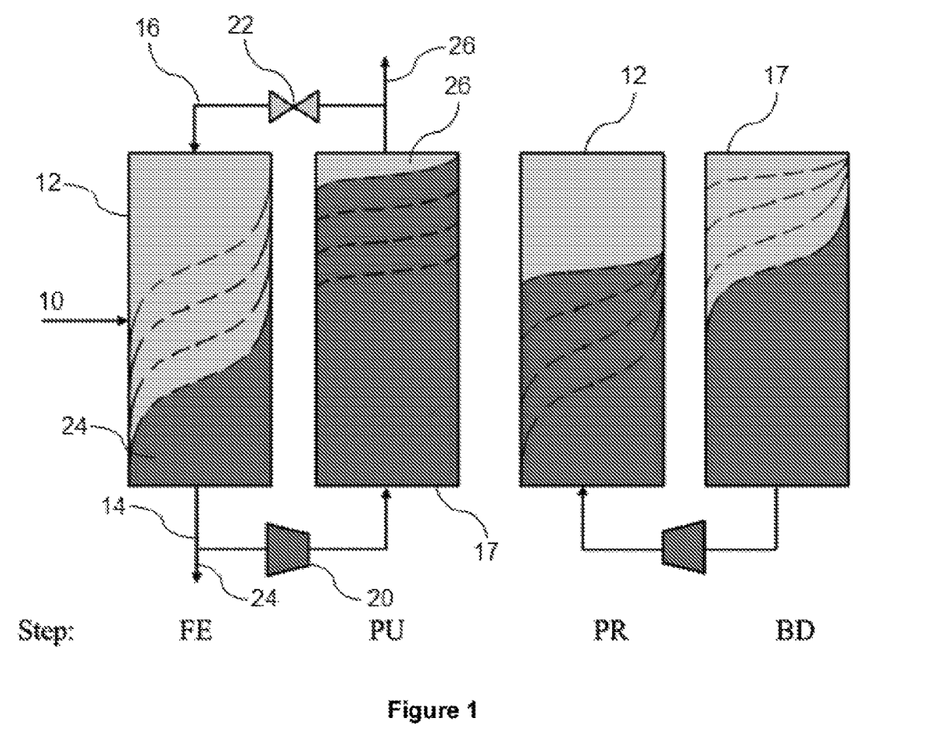
FIG. 1 is a process schematic for half of a DR-PSA cycle in a PL-A configuration.

As shown in FIG. 1, the feed stream 10 enters one of the columns (low pressure) 12 at an intermediate position, product streams are drawn from one end 14 of each column, and a reflux stream 16 enters each column at its other end. The second column 17 is at a higher pressure. The reflux streams entering a bed are taken from the product stream leaving the other bed and passed through a compressor 20 or a valve 22 to raise or lower their pressure, respectively. Within the adsorption columns, the heavy gas (CH4) is 24 and the light gas (N2) is 26.

The primary advantage of DR-PSA over conventional PSA processes is that the separation of a mixture into two components achievable with a cyclic DR-PSA process is constrained only by material balance, whereas a cyclic PSA process is additionally constrained by the ratio of the adsorbent materials' capacities at the cycles' two operating conditions (high and low pressure and/or low and high temperature). However, the material balance constraint does not ensure that the DR-PSA cycle will attain an optimal separation, which for a binary mixture is defined as either:

i. One product stream in which the mixture's dominant component reaches or exceeds the desired purity;

ii. One product stream in which the mixture's minor component reaches or exceeds the desired enrichment; and iii. The combination of (i) and (ii).

For both conventional PSA and DR-PSA cycles, the capital cost of the process is essentially determined by the number and size of the adsorbent beds, the quality of the adsorbent being used (as measured by its capacity, selectivity and longevity) as well as the equipment used to swing the pressure and temperature of the beds through the cycle. In general, the larger the capital cost, the more feed gas can be treated in a given cycle and/or the better the separation performance that is achievable, subject to the aforementioned constraints, and sufficiently judicious operation of the bed. The operating cost of these cycles is set by the amount of gas being treated in a cycle and the cost of the work necessary to force the gas to be at the desired operating conditions. For DR-PSA cycles, in addition to the combinations of bed temperatures and pressures, the reflux flow rate is a key operational parameter which impacts the cycle's operating cost.

The amount and composition of the feed gas to be treated, the quality of the adsorbent and the operating pressure and temperature of the beds are taken to be fixed and, hence, so is the cycle's capital cost.

The cycle should be operated such that it does not exceed the maximum number of moles that can be treated per bed per cycle without degrading the separation performance: this amount is denoted $n_{treated}^{(ads)}$. In practice, $n_{treated}^{(ads)}$ fixes the combination of the cycle's feed time, $t_F$, and the sum F+R of the feed (F) and reflux (R) flow rates. There is a trade-off between $t_F$ and F+R: if one is fixed and the other too large such that their combination exceeds $n_{treated}^{(ads)}$, then the product streams will be excessively contaminated and separation performance degraded. However, if the combination of $t_F$ and F+R is too small then the capital cost of the process will be larger than it needed to be for the amount of gas being treated per cycle. Therefore to optimise the capital cost of the DR-PSA cycle it is necessary to select $t_F$ and F+R such that their mathematical product is as close as possible to $n_{treated}^{(ads)}$.

In a PSA cycle the feed stream always enters at one end of the bed while in DR-PSA the feed stream can enter at any axial location. Additionally, in a PSA cycle there is no reflux stream to be combined with the feed stream, whereas in a DR-PSA cycle the reflux stream is an operating parameter that can be varied to improve the separation performance achieved for a given operating cost.

Figure 2:
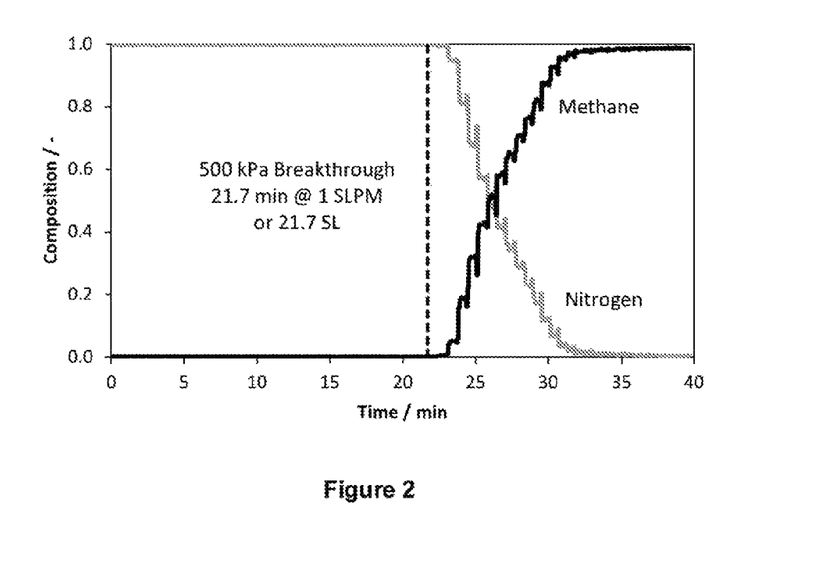
FIG. 2 depicts breakthrough profiles of $CH_4$ and $N_2$.

The values of $n_{treated}^{(ads)}$, $t_F$ and F+R can be determined in a variety of ways, including from experiment and/or by modelling. To determine the maximum number of moles that can be adsorbed in a bed, displacement tests, the results of which can be seen in FIG. 2 can be utilised. The bed is initially saturated with nitrogen at a steady state flow. At $t_0$, the nitrogen flow is stopped and methane is fed to the bed until breakthrough. Allowances for the fraction of the bed used for pressurisation and blow-down, gas phase dispersion and mass transfer zones must be included in such models. A way to achieve optimum separation performance with a DR-PSA cycle is by including the variable feed location and reflux flow rate in the determination of cycle time and feed flow for a given adsorbent bed.

To achieve an optimal separation as per (iii) above (that is the combination of (i) and (ii)), the product flow rates should be set to so that their ratios to the feed flow rate are the same as the ratios of the target components in the feed mixture composition; and the feed rate and feed composition are fixed. The amount of heavy product taken from the system automatically determines the light product flow rate. The higher the heavy product flow rate, the lower its concentration. The "optimum compromise" maximizes the concentration of both heavy and light product. Increasing the reflux flow rate (while product flow is fixed) improves product concentration, while also increasing pumping costs. However increasing reflux flow means the bed size must be increased, or else the maximum number of moles that can be adsorbed will be exceeded.

To determine the operating point with respect to heavy/light product flow rates and reflux rate, the choice is likely to be other than the "optimum compromise". For example, if the key objective is to run gas fired power station (that requires a minimum $CH_4$ concentration of e.g. 0.4), operating at point B in FIG. 3 will produce more total $CH_4$ than at point A. A smaller bed can deliver a certain volume of $CH_4$ operating at B than at A. If the key objective is to minimize greenhouse gas emissions, point C may be the chosen operating point.

Figure 3:
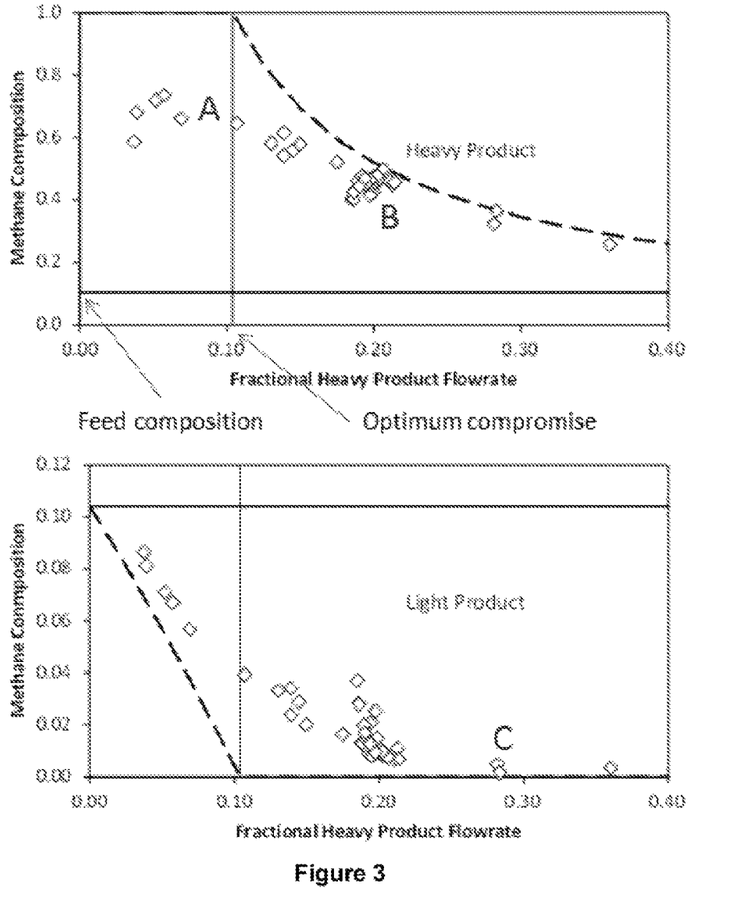
FIG. 3 depicts methane composition of heavy (top) and light (bottom) product streams as a function of the fractional (or relative) heavy product flow rate.

FIG. 3 shows the material balance constraints (dashed lines) on the heavy and light product purities for a feed mixture of $0.104CH_4+0.896N_2$, together with some example data generated by a DR-PSA cycle operating near optimally. The solid vertical and horizontal lines each intercept their respective axes at the composition of the feed gas. From this it can be seen that to (theoretically) produce a pure heavy product, the fractional heavy product flow rate has to be equal to or less than the feed composition (0.104 or 10.4%). FIG. 3 also indicates that improved enrichment of the heavy product can be achieved, at the expense of the light product purity by choosing a fractional heavy product flow rate which is less than the heavy component fraction in the feed gas: i.e. (ii) above. Similarly, a higher purity light product stream can be achieved by increasing the fractional heavy product flow rate above this threshold at the expense of the heavy product enrichment. In summary, the ratio, $p_H$ of the heavy product flowrate, H, to the feed flow rate, F, defines the separation performance, with maximum enrichment, $\varepsilon$, occurring when it is less than the partial feed flow rate of the heavy component ($p_H=H/F \leq x_{CH_4}$), and increased light product purity ($\pi$) occurring when it is higher than the partial feed flow rate of the heavy component ($p_H=H/F \geq x_{CH_4}$).

The data points shown in FIG. 3 show all of the 10.4% feed methane experiments conducted for a diverse set of operating conditions, in which variable light reflux and heavy product flow rates, different configurations (e.g. PL-A, PH-A, PL-B and PH-B, where PL refers to feed to the low pressure column, PH to the high pressure column, and "A" refers to pressure reversal via heavy end of the columns and "B" refers to that via the light end) and several different feed times have been investigated. All the experimental results fall into a relatively narrow band.

Figure 4:
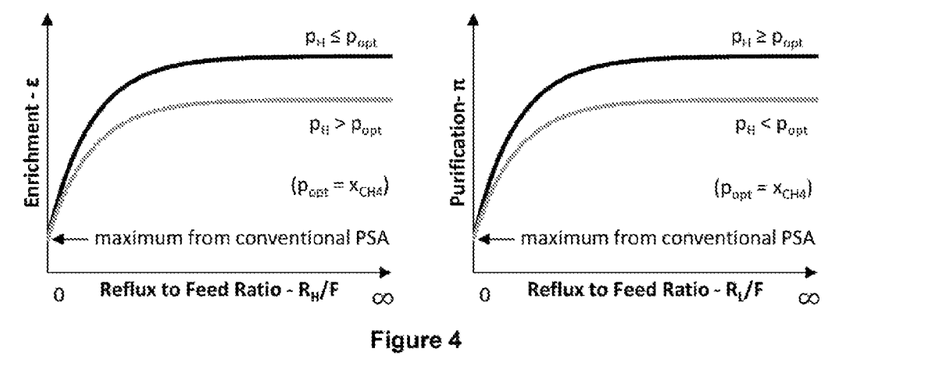
FIG. 4 represents variation of (left) the enrichment of the heavy product stream as a function of the heavy reflux to feed flow ratio; and (right) the purity of the light product stream as a function of the light reflux to feed flow ratio.

Once the value of $p_H$ has been selected (i.e. the balance between enrichment and purification desired), then there is one more operational parameter—the reflux flow rate that can be specified, which will affect the separation performance achieved. The reflux can be controlled in one of two ways—by setting the light reflux flow, $R_L$, or by setting the heavy reflux flow, $R_H$. Once one of these is set, the other is constrained; if the product flow rates are constant then increasing $R_H$ will increase $R_L$ too. It is convenient to refer to the heavy reflux flow rate when focusing on the enrichment of the heavy product (i.e. (ii) above), and on the light reflux flow rate when focusing on the purity of the light product (i.e. (i) above). In practice the reflux flow is linked to the chosen bed pressures and the throughput curve of the selected compressor; however it is possible to design a DR-PSA cycle in which the amount of reflux flow circulating is independent of the product flow rates by choosing a compressor with an adequate range of throughputs for a given pair of bed operating pressures. Importantly, it is assumed in the below that if R is increased then the value of $t_F$ is adjusted in accord with Step 1 of this method, to ensure that breakthrough does not occur and degrade the separation performance. FIG. 4 shows how for a fixed value of $p_H$ the heavy product enrichment varies with the relative heavy reflux to feed ratio, $R_H/F$, and similarly how the light product purity varies with the relative light reflux to feed ratio, $R_L/F$.

FIG. 4 represents a general illustration of the enrichment factor and purification (stripping) factor as a function of relative reflux flow rate (reflux flow divided by the feed flow) based on the understanding of the results in FIG. 3. The value of $R_H$ and $R_L$ are not independent: once one is specified, the other is fixed. Each curve shown corresponds to a fixed value of the relative heavy product flow rate, which once specified also fixes the relative light product flow rate.

FIG. 4 also shows that in the limit of no reflux flow, the performance achieved with conventional PSA cycles is achieved, which is known to be limited by the adsorbent's selectivity and the amount of void space in the adsorbent bed. By increasing the reflux flow (at constant product flow rate) higher enrichments or purities are achievable but this comes at the cost of the increased operating cost associated with the work being done with the compressor. Clearly there is a diminishing return, with the limiting separation performance achievable for a given product flow rate also set by the adsorbent quality, bed size, operating pressures and temperatures and other factors that largely determined the capital cost of the DR-PSA cycle.

The effect of the light reflux and heavy product flowrates were tested and it was found that the increase of either of these flowrates caused an increase in $N_2$ purity. However, the increased light gas purity achieved at increased heavy product flowrates was at the cost of reduced $CH_4$ enrichment as dictated by the overall mass balance.

Figure 5:
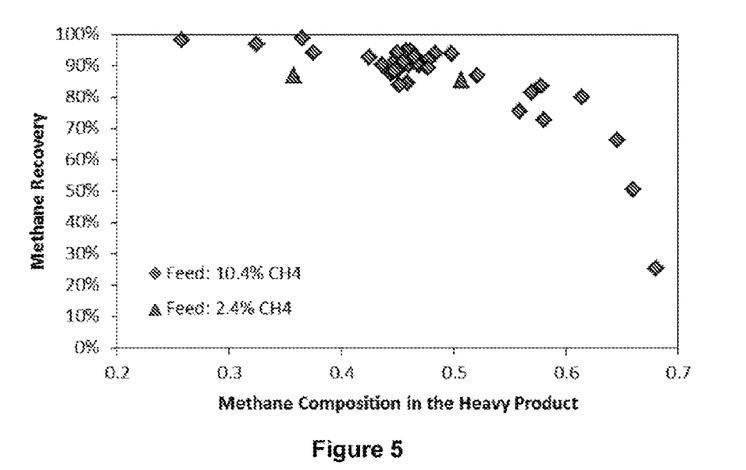
FIG. 5 depicts recovery of methane in nitrogen rich feed to DR-PSA cycle containing a standard activated carbon adsorbent material as a function of the composition of the methane-enriched heavy product stream, for two different feed concentrations.

The recovery of low concentration methane in the range of typical LNG vent gas and coal mine ventilation air, e.g. 2.4% $CH_4$ in nitrogen has been studied. The experimental results in FIG. 5 show the DR-PSA process can effectively enrich a 2.4% $CH_4$ in nitrogen mixture by 20 times with a pressure ratio of less than 4. More importantly, the methane product purity for the feed containing 2.4% $CH_4$ is comparable to that containing 10.4% $CH_4$, suggesting great enriching power of DR-PSA processes particularly for low grade methane. An important application of the present disclosure, and of DR-PSA cycles in general which has not been identified previously, is to recover or enrich methane from LNG vent gas, coal mine ventilation air, coal bed methane and the like.

Figure 6:
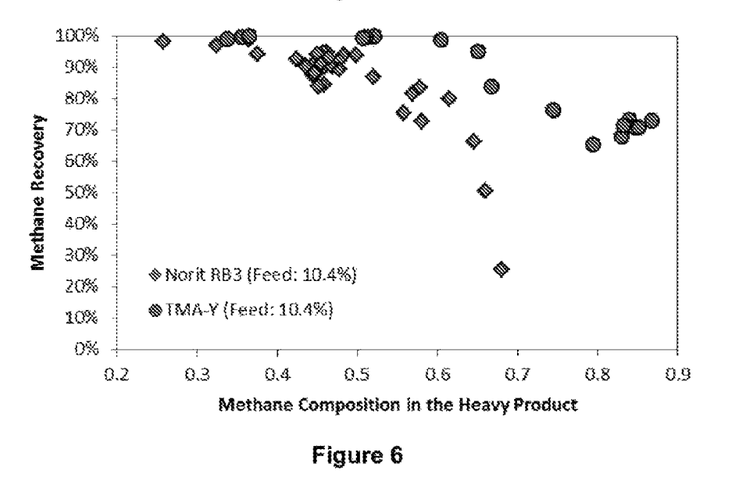
FIG. 6 depicts recovery of methane in nitrogen rich feed to a DR-PSA cycle as a function of the composition of the methane-enriched heavy product stream, for two different adsorbent materials.

The effect of adsorbents' selectivity is shown in FIG. 6 for a feed of 10.4% $CH_4$ and 89.6% $N_2$. TMA-Y, an ionic liquidic zeolite, having higher $CH_4$ over $N_2$ selectivity, obtained better $CH_4$ product purity and recovery under similar operation conditions, in comparison with activated carbon Norit RB3. Norit RB3 has a $CH_4$ over $N_2$ selectivity equilibrium selectivity of 3-4 while TMA-Y has an equilibrium selectivity of 5-8.

Figure 7:
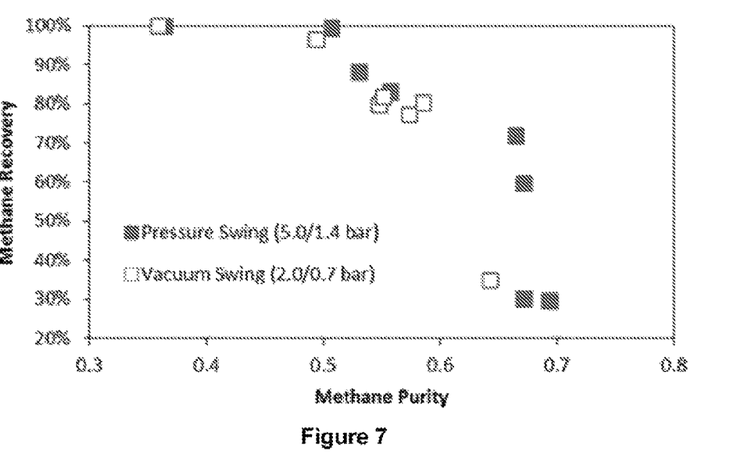
FIG. 7 depicts recovery of methane in nitrogen rich feed (10.4% $CH_4$) to a DR-PSA cycle as a function of the composition of the methane-enriched heavy product stream, using the ionic liquidic zeolite material (TMA-Y) adsorbent for both pressure swing and vacuum swing configuration.

A dual reflux vacuum swing adsorption (DR-VSA) process in which the low pressure column is operated at vacuum condition (below one absolute atmospheric pressure) and the high pressure column operates at a pressure slightly above one atm has also been studied (FIG. 7). The heavy reflux and pressure inversion steps are achieved by pulling vacuum using vacuum pump rather than compressors as in conventional DR-PSA. Results for two different modes of pressure window, namely pressure swing and vacuum swing, show that comparable separation performance can be achieved for both PSA and VSA, demonstrating the effectiveness of DR-VSA in the capture of methane from low concentration coal mine gas and other low grade low pressure sources. DR-VSA will also reduce the explosion risk in the case of $CH_4$ enrichment from coal mine air.

Figure 8:
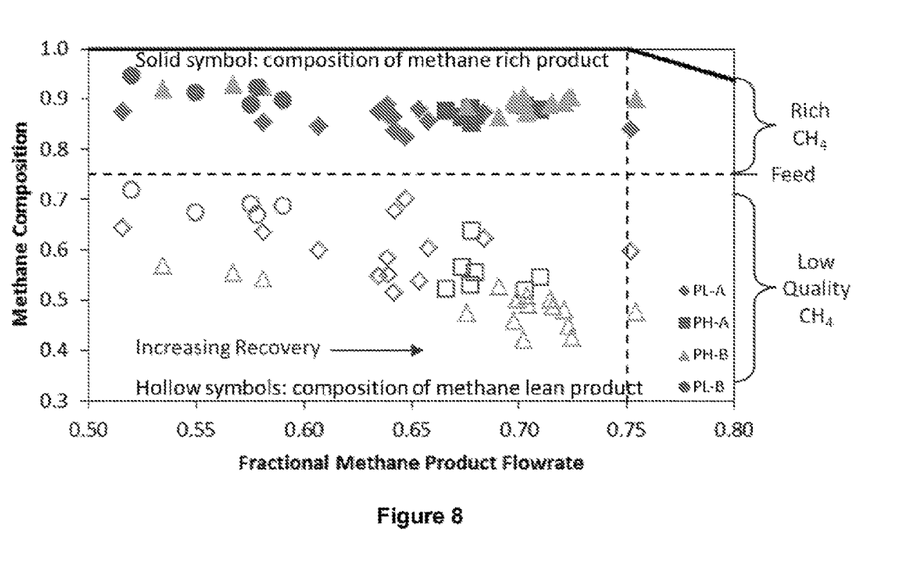
FIG. 8 depicts results for the rejection of nitrogen from a feed gas containing 75% methane using DR-PSA cycles together with a carbon molecular sieve adsorbent which is kinetically selective for $N_2$ over $CH_4$.

The separation of gas mixture with DR-PSA using kinetically selective adsorbents has been studied. As shown in FIG. 8, a carbon molecular sieve that adsorbs $N_2$ faster than $CH_4$ has been used as a $N_2$ selective adsorbent, in which a feed mixture of $0.75CH_4+0.25N_2$ was separated. Both the composition of methane rich product (in solid symbols) and the methane lean product (in hollow symbols) are shown, where rich or lean refers to comparison with feed composition; $CH_4$ recoveries of 90% were achieved with a methane rich product stream of $0.9CH_4+0.1 N_2$ and a 'waste' stream (methane lean product) of $0.5N_2+0.5CH_4$.

Figure 9:
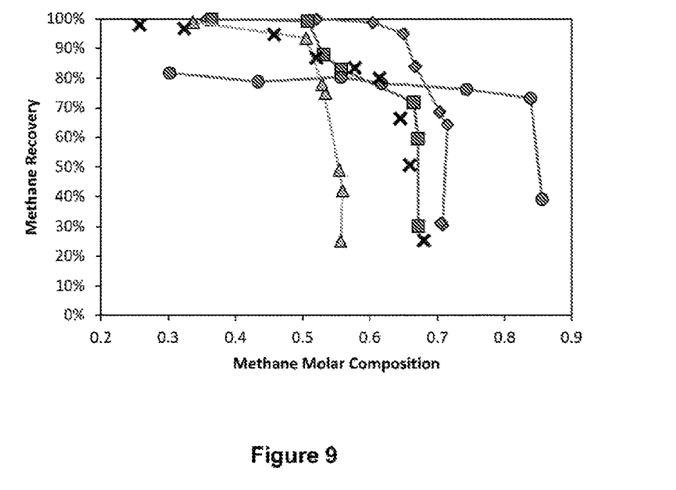
FIG. 9 is a comparison of the separation performance achieved with various DR-PSA cycles.

The Applicant conducted a number of experiments using the DR-PSA apparatus filled with the TMA-Y adsorbent material, primarily varying the feed composition, product and recycle flow rates, and which cycle configuration was employed. In addition, a total of 54 DR-PSA experiments were also conducted with the conventional activated carbon material Norit RB3 to demonstrate the superior performance of the TMA-Y adsorbent. Each experiment typically ran for about 14 hours (around 120 cycles) by which time a cyclic steady state had been achieved for several hours. The operational parameters used in the DR-PSA experiments are listed in Table 1. FIG. 9 shows a comparison of the results obtained for the same feed gas (10.4% $CH_4$) with Norit RB3 and TMA-Y in equivalent PL-A cycle configurations. The black crosses correspond to the results obtained with a conventional activated carbon (Norit RB3) configured in the PL-A cycle. The other symbols correspond to the results obtained for the TMA-Y adsorbent in the PL-A (diamonds), PH-A (squares), PL-B (triangles) and PH-B cycles (circles). These results show for the same conditions, TMA-Y is superior to Norit RB3, and that PL-A and PH-A cycles are superior to PL-B and PH-B cycles. The TMA-Y adsorbent achieved a much higher $CH_4$ recovery and much greater $CH_4$ enrichment than the Norit RB3.

TABLE 1

The default operating parameters used in the DR-PSA experiments with TMA-Y & Norit RB3.

| Feed and System Parameters | | |
|---|---|---|
| | Norit RB3 | TMA-Y |
| Feed flowrate ($F_{FE}$) | 1.25 SLPM | 1.25 SLPM |
| Temperature (ambient) | 20-25° C. | |
| High pressure ($P_H$)* | 5.0 bar | |
| Low pressure ($P_L$)* | 1.4 bar | 1.1 bar |
| Pressure ratio* | 3.57 | 4.55 |
| Fractional axial feed position ($z_F$)* | 0.5 | |
| Adsorbent Details | | |
| Material | Norit RB3 | TMA-Y |
| Pellet size (D/L) (mm) | 3/~5 | ~3/~2 |
| Mass per column | 410 g | 406 g |
| Bed void fraction | 0.433 | 0.665 |

TABLE 1-continued

The default operating parameters used in the DR-PSA experiments with TMA-Y & Norit RB3.

Cycle Parameters

| | Bed 1 | Bed 2 |
|---|---|---|
| Step I | HP Heavy Purge | LP Feed/Light Purge |
| Step II | Blowdown | Pressurisation |
| Step III | LP Feed/Light Purge | HP Heavy Purge |
| Step IV | Pressurisation | Blowdown |

Cycle Timing

| | Norit RB3 | TMA-Y |
|---|---|---|
| Steps I and III ($t_{FE/PU}$) | 120 s | 90 s |
| Steps II and IV ($t_{PR/BD}$) | | |
| A-cycles | 90 s | 90 s |
| B-cycles | 55 s | 60 s |

*These parameters were varied in some experiments

Figure 10:
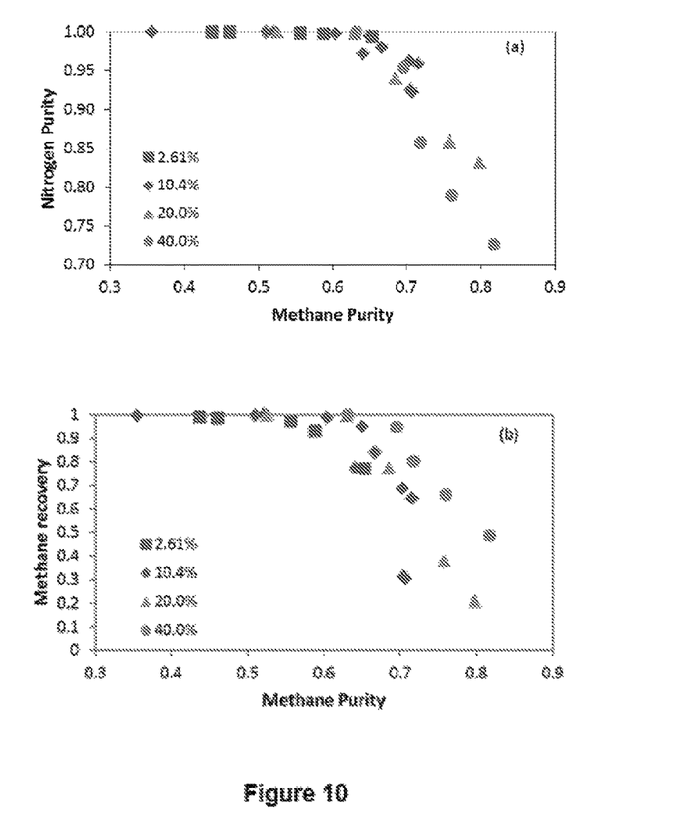
FIG. 10 is a summary of DRPSA runs in the PL-A configuration using TMA-Y adsorbents at different feed compositions.

FIG. 10 shows the separation performance achieved using a PL-A cycle with TMA-Y where the feed composition ranged from (2.6 to 40) % $CH_4$. The results are shown as a function of the $CH_4$ mole fraction in the heavy product stream and illustrate the corresponding values of (a) mole fraction purity of the $N_2$ product stream, and (b) the fractional recovery of $CH_4$ into the heavy product stream. Crucially, these data show that it is possible with the TMA-Y adsorbent in a PL-A cycle to achieve (within experimental uncertainty) a pure $N_2$ product stream and a heavy product stream containing up to 60% $CH_4$ independent of the fraction of methane in the feed stream. A similar result was achieved with PH-A cycles although, as shown in FIG. 10, the maximum $CH_4$ fraction that can be reached in the heavy product stream while still producing pure $N_2$ is reduced from about 60% to 50%. Nevertheless, since gas turbines can be operated with methane fractions as low as 25%, either of these cycles could be used in practice to achieve the project objectives, with considerations of the associated capital and operating costs of the two cycles likely to determine which should be used.

The process of the present invention can be utilised to remove methane from a 60 MMscfd $N_2$-rich vent stream generated by a cryogenic distillation process within an LNG plant (MMscfd=million standard cubic feet per day). This stream is a by-product from an LNG production train and its hydrocarbon content, which can be as low as 0.5% $CH_4$ by mole.

Throughout this specification, unless the context requires otherwise, the word "comprise" or variations such as "comprises" or "comprising", will be understood to imply the inclusion of a stated integer or group of integers but not the exclusion of any other integer or group of integers.

The invention claimed is:

1. A method for controlling gas separation of a gas mixture comprising a first component and a second component, the method comprising contacting a feed containing the gas mixture with an adsorbent in a bed in a column in a dual reflux swing adsorption process such that a first component of a gas mixture attains or exceeds a desired purity and a second component of the gas mixture attains or exceeds a desired purity, wherein the mathematical product of the cycle feed time and the sum of the molar feed flow rate and the molar reflux flow rate directed to the column does not exceed the maximum number of moles that can be treated per bed per cycle and wherein the ratio of the first product flow rate to the feed flow rate is less than or equal to the first component's fraction of the feed, and the ratio of the second product flow rate to the feed flow rate is less than or equal to the second component's fraction of the feed.

2. A method for controlling gas separation according to claim 1, wherein the product of the cycle feed time and the sum of the molar flow rates of the feed and reflux directed to the feed column is maintained as close as possible to the maximum number of moles that can be treated per bed per cycle.

3. A method for controlling gas separation according to claim 1, wherein the product of the cycle feed time and the sum of the molar flow rates of the feed and reflux directed to the feed column is maintained as close as possible to, but without exceeding, the maximum number of moles that can be treated per bed per cycle.

4. A method for controlling gas separation according to claim 1, wherein the ratios of the product flow rates to the feed flow rates are maintained at the same values as the corresponding fractions of the target components in the feed mixture composition.

5. A method for controlling gas separation according to claim 1, wherein the reflux flow rate is a sufficiently large fraction of the feed flow rate such that both the enrichment factor for the heavy component and/or the stripping factor for the light component are both not less than the ratio of the bed pressures used in the process.

6. A method for controlling gas separation according to claim 1, wherein the swing adsorption process is selected from the group of mechanisms that can be used to reverse adsorption, comprising pressure swing, thermal swing, displacement purge or nonadsorbable purge (i.e. partial pressure reduction), or a combination of the above.

7. A method for controlling gas separation according to claim 1, wherein the gas mixture includes natural gas, coal mining gas, coalbed methane, biogas, ventilation air in coal mines and nitrogen vent gas from LNG plants.

8. A method for controlling gas separation according to claim 1, wherein mixtures with a methane to nitrogen ratio of about 0.1 or greater are treated to increase the concentration of the methane component.

9. A method for controlling gas separation according to claim 1, wherein gas streams containing as little as 0.5% methane are purified by the method of the invention down to 100 ppmv methane.

10. A method for controlling gas separation according to claim 1, wherein the adsorbent has a selectivity for the first component over the second component of greater than one.

11. A method for controlling gas separation according to claim 1, wherein the adsorbent has an equilibrium selectivity for methane over nitrogen greater than 2.

12. A method for controlling gas separation according to claim 1, wherein the adsorbent has an equilibrium selectivity for methane over nitrogen greater than 5.

13. A method for controlling gas separation according to claim 1, wherein the adsorbent is kinetically selective for nitrogen over methane.

14. A method for controlling gas separation according to claim 1, wherein the adsorbent is selected from the group comprising activated carbons, zeolites and ionic-liquidic zeolites, carbon molecular sieves, clinoptilolite and combinations thereof.

15. A method for controlling gas separation according to claim 1, wherein the cycle-feed time is shorter than the characteristic sorption time of the slower and less adsorbed gas component but longer than the characteristic sorption time of the faster and more adsorbed gas component.

* * * * *